(12) United States Patent
Baror et al.

(10) Patent No.: US 7,056,283 B2
(45) Date of Patent: Jun. 6, 2006

(54) DOUBLE SLEEVE ENDOSCOPE

(75) Inventors: Yaakov Baror, Haifa (IL); Michael Voloshin, Haifa (IL); Dan Oz, Even Yehuda (IL)

(73) Assignee: Sightline Technoligies Ltd., Haifa (IL)

( * ) Notice: Subject to any disclaimer, the term of this patent is extended or adjusted under 35 U.S.C. 154(b) by 63 days.

(21) Appl. No.: 10/363,490

(22) PCT Filed: Aug. 21, 2001

(86) PCT No.: PCT/IL01/00778

§ 371 (c)(1),
(2), (4) Date: Sep. 5, 2003

(87) PCT Pub. No.: WO02/19886

PCT Pub. Date: Mar. 14, 2002

(65) Prior Publication Data

US 2004/0143161 A1    Jul. 22, 2004

(30) Foreign Application Priority Data

Sep. 4, 2000 (IL) .................................... 138237

(51) Int. Cl.
*A61B 1/00* (2006.01)
(52) U.S. Cl. .................. 600/114; 600/115; 600/140
(58) Field of Classification Search ............... 600/114, 600/115, 140
See application file for complete search history.

(56) References Cited

U.S. PATENT DOCUMENTS

| | | | |
|---|---|---|---|
| 3,279,460 A | 10/1966 | Sheldon | 128/6 |
| 3,677,262 A | 7/1972 | Zukowski | 128/6 |
| 3,895,637 A | 7/1975 | Choy | 128/348 |
| 4,066,070 A | 1/1978 | Utsugi | 128/4 |
| 4,077,610 A | 3/1978 | Masuda | 254/134.4 |
| 4,148,307 A | 4/1979 | Utsugi | 128/4 |
| 4,176,662 A | 12/1979 | Frazer | 128/6 |
| 4,207,872 A | 6/1980 | Meiri et al. | 128/4 |
| 4,321,915 A | 3/1982 | Leighton et al. | 128/4 |
| 4,403,985 A | 9/1983 | Boretos | 604/53 |
| 4,561,427 A | 12/1985 | Takada | 128/4 |
| 4,646,722 A | 3/1987 | Silverstein et al. | 128/4 |
| 4,858,001 A | 8/1989 | Milbank et al. | 358/98 |
| 4,868,644 A | 9/1989 | Yabe et al. | 358/98 |
| 4,869,238 A | 9/1989 | Opie et al. | 128/6 |
| 4,878,485 A | 11/1989 | Adair | 128/6 |
| 4,884,133 A | 11/1989 | Kanno et al. | 358/98 |
| 4,893,613 A | 1/1990 | Hake | 128/4 |
| 4,967,092 A | 10/1990 | Freignier et al. | 250/560 |
| 5,051,824 A | 9/1991 | Nishigaki | 358/98 |
| 5,090,259 A | 2/1992 | Shishido et al. | 73/866.5 |
| 5,125,143 A | 6/1992 | Takahashi | 29/237 |
| RE34,110 E | 10/1992 | Opie et al. | 128/6 |

(Continued)

FOREIGN PATENT DOCUMENTS

DE    3440177    5/1986

(Continued)

*Primary Examiner*—Beverly M. Flanagan
(74) *Attorney, Agent, or Firm*—Ladas and Parry LLP

(57) ABSTRACT

Endoscopic apparatus, including a probe (9) having an anterior component (12) and a posterior component (14), and a flexible dual-sleeved tube (31). The flexible dual-sleeved tube consists of a flexible external sleeve (26) and a flexible internal sleeve (36) within the external sleeve. The sleeves are coupled between the anterior component and the posterior component so as to define an enclosure (37) between the sleeves, which enclosure is inflated in order to propel the anterior component within a lumen (49).

21 Claims, 4 Drawing Sheets

U.S. PATENT DOCUMENTS

| | | | |
|---|---|---|---|
| 5,188,111 A | 2/1993 | Yates et al. | 128/657 |
| 5,201,908 A | 4/1993 | Jones | 128/4 |
| 5,203,319 A | 4/1993 | Danna et al. | 128/4 |
| 5,259,364 A | 11/1993 | Bob et al. | 128/4 |
| 5,301,061 A | 4/1994 | Nakada et al. | 359/362 |
| 5,365,331 A | 11/1994 | Tamburrino et al. | 356/241 |
| 5,398,670 A | 3/1995 | Ortiz et al. | 128/6 |
| 5,408,992 A | 4/1995 | Hamlin et al. | 128/4 |
| 5,483,951 A | 1/1996 | Frassica et al. | 600/104 |
| 5,489,256 A | 2/1996 | Adair | 600/133 |
| 5,496,259 A | 3/1996 | Perkins | |
| 5,538,497 A | 7/1996 | Hori | 600/182 |
| 5,586,968 A | 12/1996 | Grundl et al. | 600/114 |
| 5,674,182 A | 10/1997 | Suzuki et al. | 600/129 |
| 5,681,260 A | 10/1997 | Ueda et al. | 600/114 |
| 5,704,899 A | 1/1998 | Milo | 600/161 |
| 5,817,015 A | 10/1998 | Adair | 600/121 |
| 5,819,736 A | 10/1998 | Avny et al. | 128/653.1 |
| 5,827,177 A | 10/1998 | Oneda et al. | 600/121 |
| 6,007,482 A | 12/1999 | Madni et al. | 600/115 |
| 6,007,484 A | 12/1999 | Thompson | 600/173 |
| 6,071,234 A | 6/2000 | Takada | 600/114 |
| 6,077,219 A | 6/2000 | Viebach et al. | 600/114 |
| 6,110,103 A | 8/2000 | Donofrio | 600/121 |
| 6,110,104 A | 8/2000 | Suzuki et al. | 600/124 |
| 6,132,211 A | 10/2000 | Peithman | 433/29 |
| 6,165,123 A | 12/2000 | Thompson | 600/152 |
| 6,174,280 B1 | 1/2001 | Oneda et al. | 600/121 |
| 6,224,543 B1 | 5/2001 | Gammons et al. | |
| 6,293,907 B1 | 9/2001 | Axon et al. | |
| 6,416,462 B1 | 7/2002 | Tovey et al. | |
| 6,447,444 B1 | 9/2002 | Avni et al. | 600/121 |
| 6,485,409 B1 | 11/2002 | Voloshin et al. | 600/115 |
| 6,764,441 B1 * | 7/2004 | Chiel et al. | 600/115 |

FOREIGN PATENT DOCUMENTS

| | | |
|---|---|---|
| DE | 296 15401 | 12/1996 |
| EP | 0 338557 | 10/1989 |
| EP | 0 745 347 | 12/1996 |
| EP | 0 136 539 | 9/2000 |
| FR | 8010672 | 11/1987 |
| WO | WO 86/06944 | 12/1986 |
| WO | WO 94/05200 | 3/1994 |
| WO | WO 99/17828 | 4/1999 |
| WO | WO 00/44275 | 8/2000 |

* cited by examiner

DOUBLE SLEEVE ENDOSCOPE

FIELD OF THE INVENTION

The present invention relates generally to propulsion of objects within lumens, and specifically to methods and devices for propelling medical instruments through the colon.

BACKGROUND OF THE INVENTION

The use of an endoscope for examining a body cavity is well known in the art. The diagnostic and therapeutic advantages conferred by direct examination of the gastrointestinal tract with a flexible endoscope have made this method a standard procedure of modern medicine. One of the most common endoscopic procedures is colonoscopy, which is performed for a wide variety of purposes, including diagnosis of cancer, determination of the source of gastrointestinal bleeding, viewing a site affected by inflammatory bowel disease, removing polyps, and reducing volvulus and intussusception.

While colonoscopy is useful and effective, it is a difficult procedure for a physician to perform and is painful and occasionally dangerous for the patient. These problems stem from the need to push and steer the long, flexible colonoscope through the intestine by pushing it in from its proximal end, outside the body.

It would be desirable to provide a propulsion mechanism to push or pull the endoscope forward from its distal end, inside the body. A number of methods and devices have been proposed for this purpose, although none has achieved clinical or commercial acceptance.

U.S. Pat. No. 4,207,872 to Meiri et al., whose disclosure is incorporated herein by reference, describes a device and method for advancing an endoscope through a body passage utilizing multiple fluid-filled flexible protrusions distributed along an outer surface of a sleeve containing the endoscope. Alternately increasing and decreasing the fluid pressure within the protrusions advances the endoscope along a body passage. Each protrusion is in direct contact with an inner surface of the body passage and applies local contact pressure against this relatively small contact surface in order to propel the endoscope forward.

U.S. Pat. No. 3,895,637 to Choy, whose disclosure is incorporated herein by reference, describes a device able to move through a tubular organ by sequentially inflating and deflating first and second radially inflatable members. The inflation anchors the inflated member against a local region of the tubular organ, while air pressure in a longitudinally inflatable communicating part of the device moves the non-anchored part of the device longitudinally through the tubular organ. Sufficient contact pressure of the inflated member against a relatively small length of the tubular organ is required in order for the device to be able to progress through the organ. U.S. Pat. No. 3,895,637 has no provision to distribute the contact pressure over a larger area of the tissue against which it presses in order to generate longitudinal motion.

U.S. Pat. No. 4,321,915 to Leighton et al., whose disclosure is incorporated herein by reference, describes an everting tube device for introducing a tool into a body cavity using alternating steps of applying positive pressure to evert the tube and advance the tool, and applying a vacuum to pull the everted tube away from the tool so that an operator can retract the tool one half of the distance it advanced in the previous step. The operator using this device is required to manually withdraw the tool the prescribed distance during every pressure cycle in order to avoid causing the tool to advance too far beyond the tip of the everted tube.

U.S. Pat. No. 4,403,985 to Boretos, whose disclosure is incorporated herein by reference, describes a jet-propelled device for insertion into body passageways. Pressurized fluid is passed to the device from outside of the body and then ejected from an orifice in the device in one direction in order to propel the device in the opposite direction. The device of U.S. Pat. No. 4,403,985 thus generates propulsion by expelling material into the body passageway.

PCT patent application PCT/IL97/00077, to Lerner, whose disclosure is incorporated herein by reference, describes an endoscopic insertion device in the form of a flexible tubular semi-toroidal sheath. An endoscopic probe is inserted into the sheath, and the sheath is inserted into a lumen. Pushing on the probe causes the sheath and the probe to move into the lumen, by the sheath moving in the same way as the tracks of a tracked vehicle.

SUMMARY OF THE INVENTION

It is an object of some aspects of the present invention to provide an improved system and method for propelling an object within a lumen.

It is a further object of some aspects of the present invention to provide an improved propulsion mechanism for advancing an endoscope within a body cavity of a patient for purposes of examination, diagnosis, and treatment.

In preferred embodiments of the present invention, a section of an endoscopic probe is advanced through the lower gastrointestinal tract of a patient by inflation of a flexible dual-sleeved tube comprised in the probe. The tube comprises an external sleeve and an internal sleeve, and inflation of the tube is accomplished by inflating the space between the sleeves. Prior to inflation, the internal sleeve is stored in a compact, folded or rolled-up state, inside a stationary posterior component of the probe. The posterior component is typically coupled to a hand held device at or adjacent to the patient's anus. The external sleeve is also stored in a folded or rolled up state, inside an anterior component of the probe.

As the tube is inflated, preferably using a pressurized gas, the anterior component is propelled forward, and the dual-sleeved tube is gradually fed out between the anterior and posterior components. During this process, the portion of the external sleeve that has been fed out expands radially outward to contact the intestinal wall. This portion of the external sleeve remains substantially stationary relative to the intestinal wall while the tube is inflated. Longitudinal motion of the external sleeve relative to the wall generally occurs only in the region of the anterior component itself. The anterior component thus advances easily, and trauma to the gastrointestinal tract is minimized.

The internal sleeve feeds out at the same time as the external sleeve. The interior of the portion of the internal sleeve that has been fed out forms a passageway through which cables and tubes linking the anterior and posterior components are pulled forward by the motion of the anterior component. During motion of the anterior component there is virtually no relative motion between the cables and tubes and the internal sleeve, since both are pulled forward at substantially the same rate. Preferably, the cables carry video signals from a camera head in the anterior component to a display coupled to the posterior component, while the tubes enable endoscopic equipment or material to be passed in or out between the anus and the anterior component.

In preferred embodiments of the present invention, the head of the anterior component comprises a transparent viewing window. The window enables imaging devices, such as a miniature video camera and/or a light source, as are known in the art, to capture endoscopic images. Means for operating the imaging devices, such as wires and/or fiber-optic lines, pass through the internal sleeve and so do not contact the external sleeve of the tube.

To remove the probe, the space between the sleeves is deflated and the tube is pulled out through the anus.

Advancing the probe through the gastrointestinal tract by inflating the dual-sleeved tube reduces or eliminates the necessity of applying mechanical force at the proximal end of the probe (outside the patient's body) in order to insert the probe, as is required using conventional endoscopes. The present invention thus reduces or eliminates the necessity of applying concentrated, local pressure to any part the patient's body, reduces or eliminates rubbing and friction between the probe or parts of it and the patient's body, and avoids ejecting fluids or other materials into the body passageway. Furthermore, the dual-sleeved tube reduces or eliminates damage or trauma to the external sleeve or to the colon wall by insulating movement of endoscopic equipment from the external sleeve.

There is therefore provided, according to a preferred embodiment of the present invention, endoscopic apparatus, including:

a probe including an anterior component and a posterior component; and a flexible dual-sleeved tube, including a flexible external sleeve and a flexible internal sleeve within the external sleeve, coupled between the anterior component and the posterior component so as to define an enclosure between the sleeves, which enclosure is inflated in order to propel the anterior component within a lumen.

Preferably, the apparatus includes an imaging device inserted within the anterior component which captures an image of the lumen.

Further preferably, the apparatus includes a handle which removably mates with the posterior component so as to enable an operator to hold the posterior component in a generally stationary position.

Preferably, the internal sleeve includes a passageway for conveying endoscopic equipment between the anterior and posterior components.

Preferably, the apparatus includes at least one tube fixedly connected to the anterior component and residing within the internal sleeve.

Preferably, the at least one tube is substantially stationary relative to a section of the internal sleeve.

Further preferably, a section of the external sleeve is substantially stationary relative to a wall of the lumen.

Preferably, the anterior component includes an anterior-component chamber, and the dual-sleeved tube includes an anterior-component portion which is held in a compact state within the anterior-component chamber and which feeds out from a proximal end of the anterior component as the anterior component is propelled within the lumen.

Preferably, the anterior component includes a head section and a flexible sleeve coupling the anterior-component chamber to the head section, which sleeve enables the head section to be oriented.

Further preferably, the dual-sleeved tube inlcudes a posterior-component portion which is held in a compact state coupled to the posterior component and which feeds out from a distal end of the posterior component as the anterior component is propelled within the lumen.

Preferably, the enclosure is a gas-tight enclosure which is inflated by a fluid in order to propel the anterior component within the lumen.

Preferably, the fluid is an inert gas.

Alternatively, the fluid is an inert liquid.

There is further provided, according to a preferred embodiment of the present invention, a method for propelling an endoscopic probe component within a lumen, including:

providing an anterior and a posterior component of the probe;

coupling between the anterior component and the posterior component a dual-sleeved tube including a flexible external sleeve and a flexible internal sleeve within the external sleeve, so as to define an enclosure between the sleeves; and inflating the enclosure to advance the anterior component through the lumen.

Preferably, inflating the enclosure includes inflating the enclosure such that a section of the external sleeve remains substantially stationary relative to a wall of the lumen as the anterior component advances.

Preferably, the method includes coupling one or more tubes to the anterior component, and inflating the enclosure includes maintaining the one or more tubes substantially stationary relative to the internal sleeve as the anterior component advances.

Preferably, providing the anterior component includes providing an anterior-component chamber within the anterior component, and coupling the dual-sleeved tube includes storing a portion of the tube in the anterior-component chamber.

Preferably, coupling the dual-sleeved tube includes storing a portion of the tube in the posterior component.

Preferably, the method includes imaging a section of the lumen with a camera assembly coupled to the anterior component.

Further preferably, the method includes removably mating the posterior component with a handle so as to enable an operator to hold the posterior component in a generally stationary position.

The present invention will be more fully understood from the following detailed description of the preferred embodiments thereof, taken together with the drawings, in which:

DETAILED DESCRIPTION OF PREFERRED EMBODIMENTS

Figure 1:
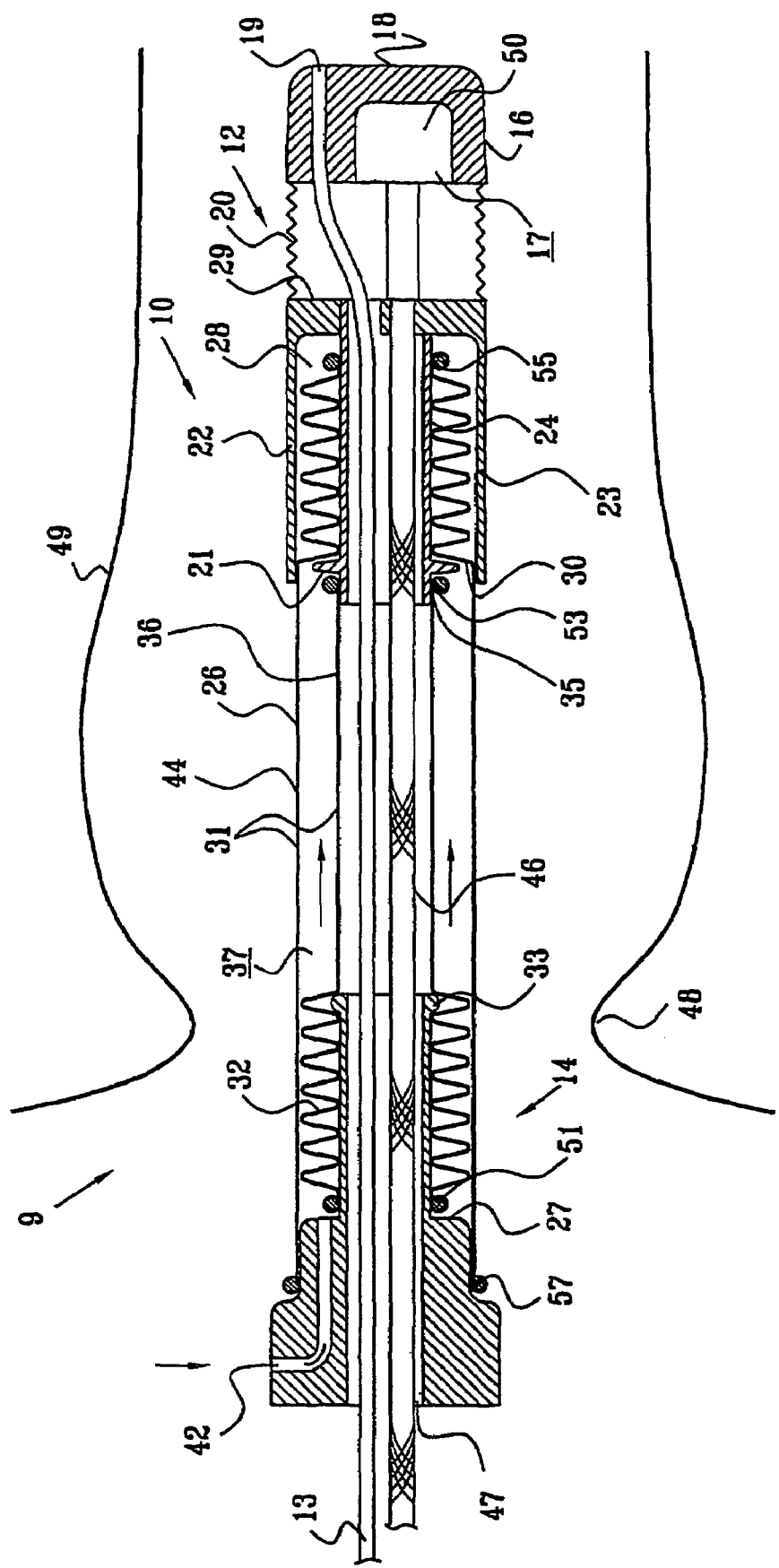
FIG. 1 is a schematic, sectional drawing of an outer section of an endoscopic probe, according to a preferred embodiment of the present invention.

Reference is now made to FIG. 1, which is a schematic sectional drawing of an outer section 10 of an endoscopic probe 9, according to a preferred embodiment of the present invention. Section 10 comprises an anterior component 12, which is propelled forward into a lumen or other passage 49, and a posterior component 14 which remains in a substantially stationary position outside lumen 49. Typically lumen 49 is the colon of a patient, and probe 9 is use to perform an endoscopic procedure, as described further hereinbelow. Components 12 and 14 are generally circular in cross-section.

Anterior component 12 comprises a cylindrical head 16, closed at its distal end by a transparent viewing window 18. Head 16 comprises a recess 17 at the proximal side of window 18, within which recess a camera of a camera assembly 50 may be positioned. Camera assembly 50 is described hereinbelow with reference to FIG. 2, and for clarity assembly 50 is not shown in detail in FIG. 1. Assembly 50 and recess 17 are constructed so that the assembly mates with the recess. Anterior component 12 comprises one or more openings 19, to which respective one or more tubes 13 are fixedly attached, so that respective passages are formed by the tubes to the distal side of head 16.

Anterior component 12 further comprises a semi-rigid sleeve 20. Sleeve 20 is fixedly attached between the proximal end of head 16 and the distal end of a tube-holder 23 comprised in component 12. Tube-holder 23 comprises an outer cap 22 having an internal flange 29 at its distal end, which flange is fixedly attached to an inner spindle 24. Spindle 24 comprises an external protrusion 21 close to its proximal end, the protrusion having an external radius less than the internal radius of cap 22, so that a circular slot 30 is formed between the flange and the cap. Also, a cylindrical chamber 28 is formed between cap 22 and spindle 24.

Posterior component 14 comprises a spindle 32 having an external flange 27 at its proximal end. Spindle 32 and inner spindle 24 are implemented to have substantially similar internal radii. Spindle 32 comprises an external protrusion 33 at its distal end. A vent 42 is formed in flange 27.

Section 10 further comprises a dual-sleeved tube 31. Tube 31 comprises a flexible external sleeve 26 and, within the external sleeve, a flexible internal sleeve 36. The proximal end of sleeve 26 is fixedly attached to an external surface of flange 27, preferably by an O-ring 57, so as to form a gas-tight seal at end 25. The distal end of sleeve 26 is fixedly attached, preferably by an O-ring 55 gripping spindle 24, to the proximal side of flange 29, within chamber 28, so as to form a gas-tight seal. Prior to using section 10, a distal section of external sleeve 26 is stored in a folded or rolled-up compact state in anterior component chamber 28.

The distal end of internal sleeve 36 is fixedly attached to the proximal side of protrusion 21 of anterior component 12, at an internal edge 35 of spindle 24, so as to form a gas-tight seal. The proximal end of sleeve 36 is fixedly attached to the distal side of flange 27, so as to form a gas-tight seal. Preferably, the gas-tight seals at the distal and proximal ends of sleeve 36 are formed by an O-ring 53 and an O-ring 51 respectively. In some preferred embodiments of the present invention, some or all of O-rings 57, 55, 53, and 51, are replaced and/or supplemented by other sealing devices known in the art, such as glue. Prior to using section 10, a proximal section of internal sleeve 36 is stored in a folded or rolled-up compact state over spindle 32, on the proximal side of protrusion 33.

It will be appreciated that dual-sleeved tube 31 couples anterior component 12 to posterior component 14, and that an enclosure 37 formed between the sleeves of tube 31 is a gas-tight enclosure.

In order to propel component 12 into lumen 49, enclosure 37 is inflated via vent 42 with an inert gas such carbon dioxide. Alternatively enclosure 37 is inflated with an inert liquid such as sterile water. The inflation of enclosure 37 causes the compacted sections of both the internal and external sleeves to unfold and feed out over protrusion 33 and from slot 30 respectively. Thus tube 31 increases in length, and if component 14 is maintained substantially stationary outside lumen 49, typically close to a patient's anus 48, component 12 is propelled into the lumen.

As enclosure 37 is inflated, component 12 moves within lumen 49, pulling the one or more tubes 13 attached to component 12 within the lumen. During the process of inflation, a portion 44 of sleeve 26, formed by external sleeve 26 feeding out from chamber 28, expands radially and may contact the wall of lumen 49. However, portion 44 remains substantially fixed in a longitudinal direction, since sleeve 26 is fixedly attached to posterior component 14. Thus rubbing and trauma to the wall of the lumen are minimized.

Similarly, a portion 46 of sleeve 36, formed by internal sleeve 36 feeding out over protrusion 33, moves radially inward during the inflation process. Since internal sleeve 36 is fixedly attached to anterior component 12, the sleeve moves longitudinally at substantially the same rate as component 12. Thus, there is substantially no relative motion between the one or more tubes 13 and internal sleeve 36, so that the risk of potential damage due to motion between the tubes and the internal sleeve is substantially reduced.

As enclosure 37 is inflated, a passageway 47, connecting anterior component 12 to posterior component 14, is formed within internal sleeve 36.

Figure 2:
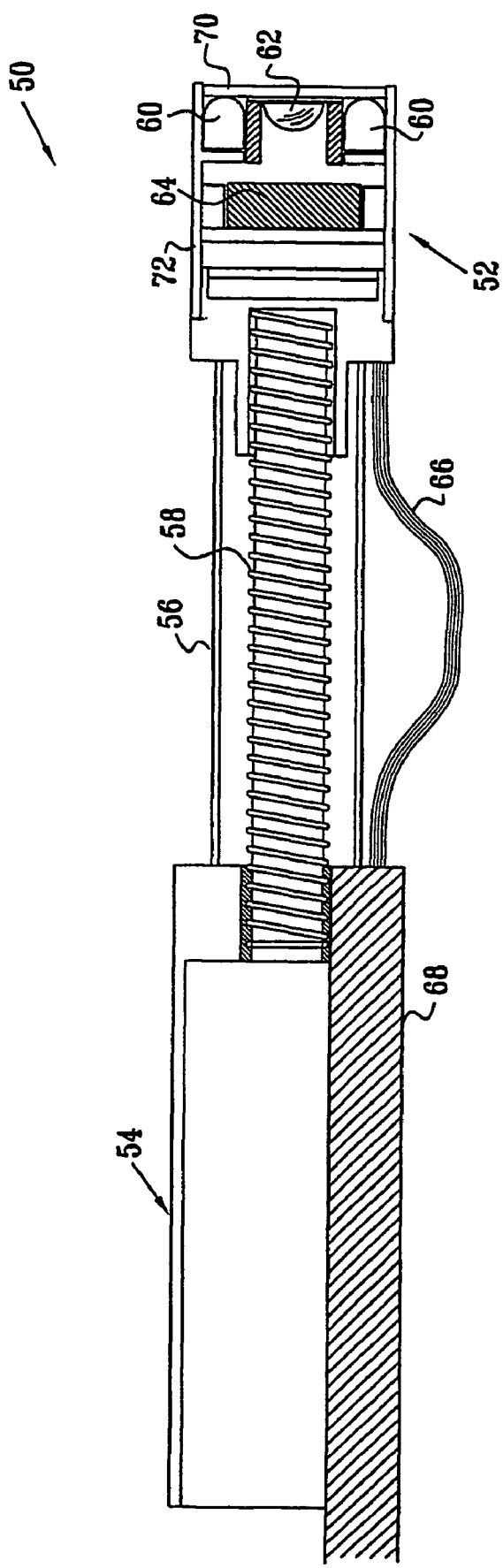
FIG. 2 is a schematic sectional drawing of a camera assembly comprised in the endoscopic probe of FIG. 1, according to a preferred embodiment of the present invention.

FIG. 2 is a schematic sectional drawing of a camera assembly 50 comprised in endoscopic probe 9, according to a preferred embodiment of the present invention. Before inserting the probe into lumen 49, assembly 50 is inserted into passageway 47, as shown in more detail in FIG. 3 below. The camera assembly is used for generating images from within the lumen. Assembly 50 preferably comprises a charge coupled device (CCD) camera 52, which is fixedly mounted to a spring 58 at the spring's distal end. Spring 58 is fixedly connected at its proximal end to the distal end of a semi-rigid, generally cylindrical guide 54.

CCD camera 52 preferably comprises a CCD array 64, on which an image of the lumen wall is formed by an objective 62. CCD array 64 and objective 62 are mounted in a housing 72, the outer surface of which is formed so as to mate with recess 17. Housing 72 comprises a transparent window 70 via which light is projected to illuminate the lumen and via which objective 62 receives the light. Lamps 60, mounted within housing 72, are used to generate the light needed. Lamps 60 and CCD array 64 are powered by wires 66 which are fed through a wire shield 68 and pass out through the proximal end of guide 54. In addition to being held by spring 58, camera 52 is fixedly attached to a plurality of rigid wires 56, which slideably feed though cylindrical channels in guide 54 to the proximal end of guide 54. Guide 54 also comprises open-sided channels which are able to accommodate the one or more tubes 13, as described in more detail below with respect to FIG. 3.

Figure 3:
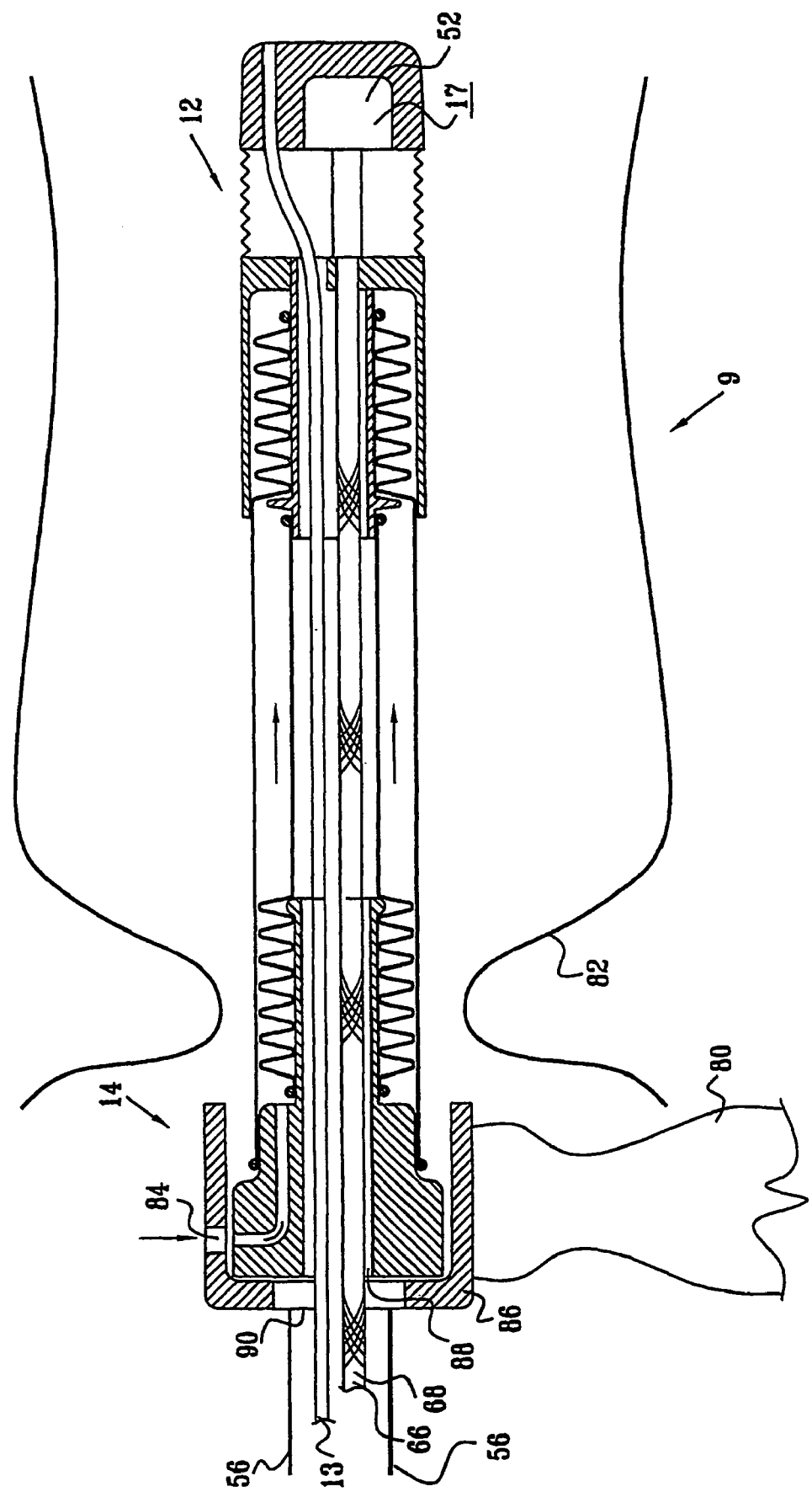
FIG. 3 is a schematic sectional drawing of the endoscopic probe of FIG. 1 in an assembled form, according to a preferred embodiment of the present invention.

FIG. 3 is a schematic sectional drawing of endoscopic probe 9 in an assembled form, according to a preferred embodiment of the present invention. In FIG. 3 probe 9 is assumed to be used in an investigation of a gastrointestinal tract 82 of a patient, although it will be understood that the probe can be used to investigate other lumens or passages. Prior to inflation of enclosure 37, assembly 50 is inserted into outer section 10. Posterior component 14 of section 10 is then inserted into a mating section 86 of a handle 80, and is fixedly held therein by the handle. Section 86 has an opening 84 which mates with vent 42, so that inflation of enclosure 37 is accomplished via opening 84. Also prior to inflation, tubes 13 and wires 66 in shield 68 are fed through an open central portion 88 of posterior component 14 and through an open proximal end 90 of mating section 86. Wires 66 are connected to a video monitor (not shown) for imaging the inside of tract 82.

As enclosure 37 is inflated, anterior component 12 moves through tract 82 as described above, and the one or more tubes 13 and wire shield 68 are pulled along with component 12 and assembly 50 into the tract. Preferably tubes 13 are used, inter alia, for the purposes of irrigation or evacuation from tract 82. Wires 56 are manipulated to orient camera 52 in different directions, as required by an operator, causing sleeve 20 to flex accordingly. The proximal ends of wires 56 exit to handle 80, enabling the operator to manipulate the wires using suitable controls in order to orient camera 52. Once camera 52 is correctly oriented, the one or more tubes 13 may be used to transfer endoscopic equipment, such as a biopsy probe, to the distal side of anterior component 12 and so to a site imaged by the camera. It will be appreciated that while enclosure 37 is inflated, motion of objects such as assembly 50 or probes within tubes 13 is insulated from tract 82 by double-sleeved tube 31, so that discomfort to the patient is minimized.

To remove endoscope 9 from tract 82, assembly 50 is withdrawn via passageway 47. Enclosure 37 is then deflated, and anterior component 12 is withdrawn from tract 82 by pulling on the one or more tubes 13.

Figure 4:
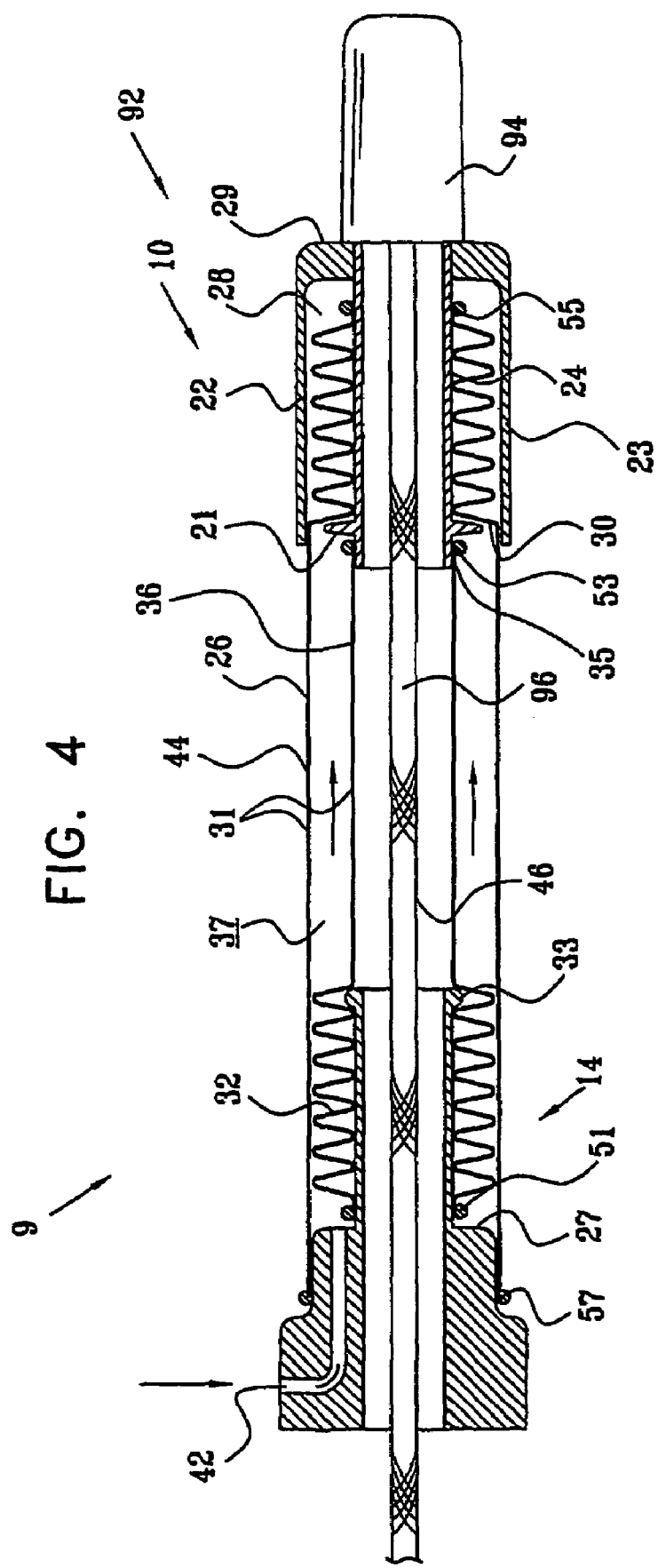
FIG. 4 is a schematic sectional drawing of an alternative endoscopic probe, according to a preferred embodiment of the present invention.

FIG. 4 is a schematic sectional drawing of an alternative endoscopic probe 92, according to a preferred embodiment of the present invention. Apart from the differences described below, the operation of probe 92 is generally similar to that of probe 9 (FIG. 1), so that elements indicated by the same reference numerals in both probes 9 and 92 are generally identical in construction and in operation. In probe 92, head 16 and semi-rigid sleeve 20 are not implemented. A sealed endoscopic camera 94, preferably coupled by wires 96 passing through passageway 47 and posterior component 14 to an external monitor, is positioned on the distal side of flange 29. Most preferably, camera 94 has an outside diameter smaller than the outside diameter of cap 22, and an inside diameter greater than the inside diameter of spindle 24. In this case, as enclosure 37 is inflated, anterior component 12 moves into lumen 49 and pushes camera 94 ahead of itself.

It will be appreciated that preferred embodiments of the present invention are implemented so that components contacting walls of a lumen, or having a possibility of contacting a biologically sensitive region, are formed from biocompatible materials such as inert plastic or stainless steel. In some preferred embodiments of the present invention, a plurality of sections 10 are implemented in a disposable, non-reusable form, so that after one section 10 has been used it is discarded and replaced. For example, in probe 9 the more costly assembly 50 with camera 52 can be reused without the need for sterilization, since it is entirely protected from contact with the patient's body by section 10.

Although preferred embodiments of the present invention are described hereinabove with reference to moving an endoscopic probe through a body lumen, it will be understood that the novel principles of the present invention may be used to move objects in lumens and other regions for non-medical applications. An example of a non-medical application includes examination within a highly corrosive or high-temperature environment, where it is not desirable to have moving parts of a propulsion unit or an instrument package exposed to the environment. It will be appreciated that for non-medical applications such as the example herein, some or all of probe 9 is implemented from materials substantially inert to the environment wherein the probe is operated. It is also to be understood that the propulsion unit and instrument package in the example above can be powered by batteries and can store data and/or transmit data by wireless communications, as is known in the art.

PCT patent application PCT/IL00/00017, which is assigned to the assignee of the present patent application, and whose disclosure is incorporated herein by reference, describes an endoscopic probe that is propelled in a lumen by a single inflatable sleeve, rather than a dual sleeve as described herein. Certain features of the probe described in this PCT application may be implemented, mutatis mutandis, in the dual-sleeve device of the present invention.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and at least one tube fixedly connected to the anterior component and residing within the internal sleeve.

2. Apparatus according to claim 1, and comprising an imaging device inserted within the anterior component which captures an image of the lumen.

3. Apparatus according to claim 1, and comprising a handle which removably mates with the posterior component so as to enable an operator to hold the posterior component in a generally stationary position.

4. Apparatus according to claim 1, wherein the internal sleeve comprises a passageway for conveying endoscopic equipment between the anterior and posterior components.

5. Apparatus according to claim 1, wherein the at least one tube is substantially stationary relative to a section of the internal sleeve.

6. Apparatus according to claim 1, wherein the external sleeve has one end connected to the anterior component and an opposite end connected to the posterior component.

7. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and wherein a section of the external sleeve is substantially stationary relative to a wall of the lumen.

8. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and wherein the anterior component comprises an anterior-component chamber, and wherein the dual-sleeved tube comprises an anterior-component portion which is held in a compact state within the anterior-component chamber and which feeds out from a proximal end of the anterior component as the anterior component is propelled within the lumen.

9. Apparatus according to claim 8, wherein the anterior component comprises a head section and a flexible sleeve coupling the anterior-component chamber to the head section, which sleeve enables the head section to be oriented.

10. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and wherein the dual-sleeved tube comprises a posterior-component portion which is held in a compact state coupled to the posterior component and which feeds out from a distal end of the posterior component as the anterior component is propelled within the lumen.

11. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and wherein the enclosure is a gas-tight enclosure which is inflated by a fluid in order to propel the anterior component within the lumen.

12. Apparatus according to claim 11, wherein the fluid is an inert gas.

13. Apparatus according to claim 11, wherein the fluid is an inert liquid.

14. A method for propelling an endoscopic probe component within a lumen, comprising the steps of: providing an anterior and a posterior component of the probe; coupling between the anterior component and the posterior component a dual-sleeved tube; forming said dual-sleeved tube as a flexible external sleeve and a separate flexible internal sleeve within the external sleeve so as to define an enclosure between the sleeves; and inflating the enclosure to advance the anterior component through the lumen, and coupling one or more tubes to the anterior component, and wherein inflating the enclosure comprises maintaining the one or more tubes substantially stationary relative to the internal sleeve as the anterior component advances.

15. A method for propelling an endoscopic probe component within a lumen, comprising the steps of: providing an anterior and a posterior component of the probe; coupling between the anterior component and the posterior component a dual-sleeved tube; forming said dual-sleeved tube as a flexible external sleeve and a separate flexible internal sleeve within the external sleeve so as to define an enclosure between the sleeves; and inflating the enclosure to advance the anterior component through the lumen. wherein said step of providing the anterior component comprises providing an anterior-component chamber within the anterior component, and wherein coupling the dual-sleeved tube comprises storing a portion of the tube in the anterior-component chamber.

16. A method according to claim 15, wherein inflating the enclosure comprises inflating the enclosure such that a section of the external sleeve remains substantially stationary relative to a wall of the lumen as the anterior component advances.

17. A method for propelling an endoscopic probe component within a lumen, comprising the steps of: providing an anterior and a posterior component of the probe; coupling between the anterior component and the posterior component a dual-sleeved tube; forming said dual-sleeved tube as a flexible external sleeve and a separate flexible internal sleeve within the external sleeve so as to define an enclosure between the sleeves: and inflating the enclosure to advance the anterior component through the lumen, wherein said step of coupling the dual-sleeved tube comprises storing a portion of the tube in the posterior component.

18. A method according to claim 17, and comprising imaging a section of the lumen with a camera assembly coupled to the anterior component.

19. A method according to claim 17, and comprising removably mating the posterior component with a handle so as to enable an operator to hold the posterior component in a generally stationary position.

20. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and wherein the external sleeve and the internal sleeve each has a first end connected to the anterior component and an opposite second end connected to the posterior component, the first end of the external sleeve being connected to the anterior component at a different location than the first end of the internal sleeve, and the second end of the external sleeve being connected to the posterior component at a different location than the second end of the internal sleeve.

21. Endoscopic apparatus, comprising: a probe comprising an anterior component and a posterior component; and a flexible dual-sleeved tube, comprising a flexible external sleeve and a separate flexible internal sleeve disposed within the external sleeve, the flexible dual-sleeved tube being coupled between the anterior component and the posterior component so as to define an enclosure between the sleeves, which enclosure is inflated in order to propel the anterior component within a lumen, and wherein the anterior component comprises a semi-rigid sleeve.

* * * * *